United States Patent [19]

Koizumi et al.

[11] Patent Number: 5,251,629

[45] Date of Patent: Oct. 12, 1993

[54] INSPECTION METHOD AND APPARATUS UTILIZING NUCLEAR MAGNETIC RESONANCE

[75] Inventors: Hideaki Koizumi, Katsuta; Kazuya Sukegawa, Ibaraki, both of Japan

[73] Assignee: Hitachi, Ltd., Tokyo, Japan

[21] Appl. No.: 915,400

[22] Filed: Jul. 20, 1992

Related U.S. Application Data

[63] Continuation of Ser. No. 602,636, Oct. 24, 1990, abandoned.

[30] Foreign Application Priority Data

Oct. 27, 1989 [JP] Japan .................................. 1-278405

[51] Int. Cl.$^5$ ............................................. A61B 5/055
[52] U.S. Cl. ............................... 128/653.2; 128/653.5; 324/309; 324/318
[58] Field of Search ................ 128/653.5, 653.2, 869, 128/874, 876; 324/318, 309

[56] References Cited

U.S. PATENT DOCUMENTS

| | | | |
|---|---|---|---|
| 4,400,820 | 8/1983 | O'Dell et al. ........................ | 128/869 |
| 4,694,837 | 9/1987 | Blakeley et al. ..................... | 128/653 |
| 4,841,965 | 6/1989 | Jacobs ................................ | 128/869 |
| 4,891,596 | 1/1990 | Mitomi ............................... | 324/318 |
| 4,979,519 | 12/1990 | Chavarria et al. .................. | 128/857 |
| 5,030,915 | 7/1991 | Boskamp et al. ................... | 324/318 |

Primary Examiner—Ruth S. Smith
Attorney, Agent, or Firm—Antonelli, Terry, Stout & Kraus

[57] ABSTRACT

A method of and an apparatus for inspecting a physical portion having physiological movement, for example, the abdominal region moving with breathing, by utilizing nuclear magnetic resonance. The circumstances of that area of the surface of the abdominal region which exists on a plane indicative of a slice to be imaged, is made different from the circumstances of the surface of the remaining physical portion. In this case, a person to be inspected feels a foreign matter at the abdominal region, and suppresses the movement of the abdominal region due to breathing, consciously and unconsciously, thereby moving the breast with breathing. Thus, the to-be-inspected abdominal region is kept quiet, and an accurate inspection can be made in a short period of time.

14 Claims, 5 Drawing Sheets

INSPECTION METHOD AND APPARATUS UTILIZING NUCLEAR MAGNETIC RESONANCE

This application is a continuation of application Ser. No. 07/602,636, filed Oct. 24, 1990, now abandoned.

BACKGROUND OF THE INVENTION

The present invention relates to the inspection method and apparatus utilizing nuclear magnetic resonance, and more particularly to a method and an apparatus for inspecting those physical portions of a person to be inspected which move together with the breathing of the patient, such as the abdominal region and the cervical region, by forming tomograms of these portions on the basis of a nuclear magnetic resonance phenomenon.

In a case where a tomogram is formed by multiple-echo magnetic resonance imaging (hereinafter referred to as "MRI"), when an object to be imaged moves, a false image is formed, and thus the tomogram cannot be used for inspection. For example, the abdominal region of a person moves unceasingly with breathing. Accordingly, to achieve a tomogram of the abdominal region, the movement of the abdominal region is suppressed by wrapping the entire abdominal region in something or by binding the abdominal region tightly with a bandage. Such methods inflict pain on a person to be inspected. Further, it is impossible to suppress the movement of the abdominal region due to breathing, completely during a period when an imaging operation is performed on the abdominal region (for example, a period of 15 to 20 minutes). Thus, it is impossible to remove the false image completely from the tomogram.

Further, a method has been proposed, in which the movement of the abdominal region is detected, and the algorithm of an imaging sequence is modified on the basis of the detected movement so that the false image is removed from the tomogram. For example, a belt provided with a tension sensor is wound around the abdominal region, and an echo signal is used only in a period between a time when exhalation has been completed and a time when air is again inhaled (that is, a period when the abdominal region stands still) is used for forming a tomogram. According to this method, the false image can be removed, but it takes a lot of time to form the tomogram. Although the abdominal region is usually inspected in a time span of 15 to 20 minutes, the above method requires an imaging time more than 30 minutes.

SUMMARY OF THE INVENTION

It is a first object of the present invention to provide a method and an apparatus for forming a tomogram of a physical portion having physiological movement such as breathing by magnetic resonance imaging in a short time without producing a false image, to inspect the physical portion accurately.

It is a second object of the present invention to provide a method and an apparatus for forming a tomogram of a physical portion by magnetic resonance imaging in such a manner that the pain given to a person which is to be inspected, is reduced to a minimum.

It is a third object of the present invention to provide an imaging-operation assisting device which can attain the first and second objects by using a minimum number of parts, is easy to operate, and does not require much labor for maintenance.

In order to attain the above objects, according to the present invention, the inspection due to magnetic resonance imaging is carried out in a state that the circumstances (such as pressure, temperature and feel) at a part or the whole of the surface of a physical region which always moves physiologically and is to be inspected, are made different from the circumstances at the surface of the remaining physical region. According to this method, a person to be inspected feels a foreign matter at the surface of the physical region which is to be imaged, such as the abdominal region. When the person feels such a foreign matter, the person suppresses the respiratory movement of a physical portion where the foreign matter is felt, and breathes by moving another physical portion.

This phenomenon has been determined on the basis of clinical experiences over a long time period. In general, a woman breathes in the breast, and a man carries out abdominal breathing. However, they can breathe by using various muscles which exist within a range from the breast to the hypogastric region. Thus, the above phenomenon can be observed.

When the movement of a physical portion which is to be imaged, and its neighborhood is suppressed by using the above phenomenon, and breathing is carried out by moving another physical portion, the degradation of the picture image of a tomogram due to breathing is lessened. Thus, an accurate inspection can be made.

DESCRIPTION OF THE PREFERRED EMBODIMENTS

Now, embodiments of the present invention will be explained, with reference to the drawings.

Figure 4:
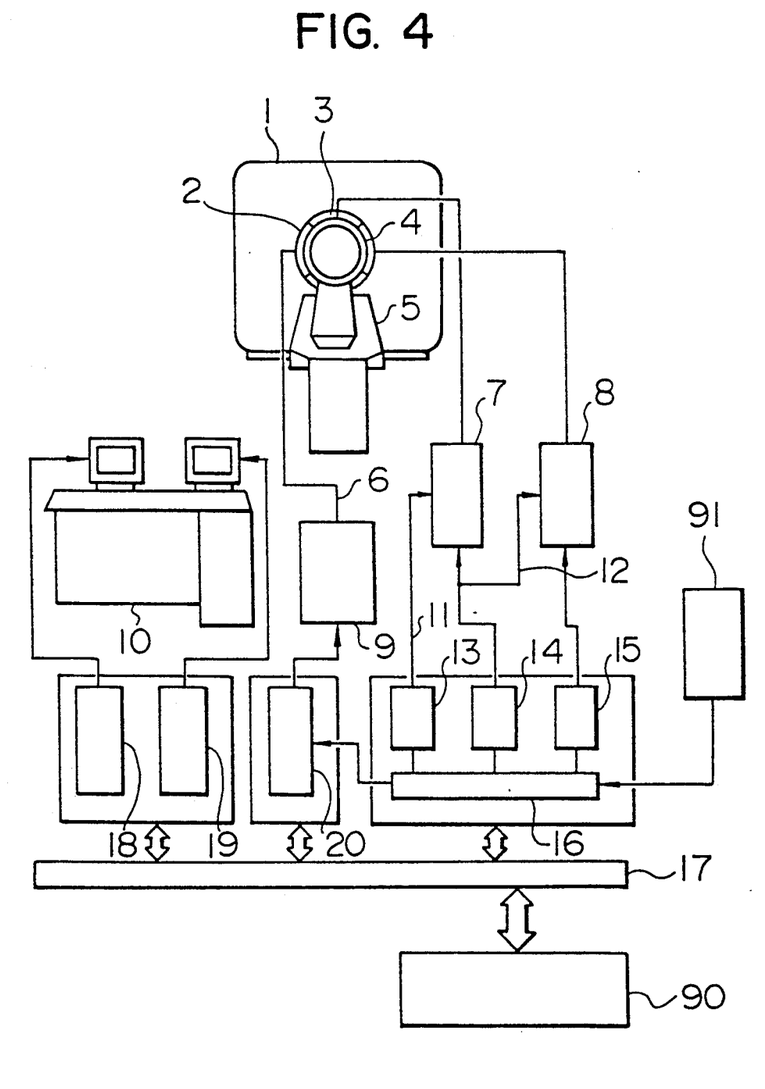
FIG. 4 is a schematic diagram showing the whole construction of an MRI apparatus.

Referring to FIG. 4, a magnet 1 is a main part of the apparatus. One of a super-conducting magnet, a normal conducting magnet and a permanent magnet is used as the magnet 1. A case where a super-conducting magnet is used, will be explained below, by way of example. In this case, the intensity of a magnetic field is 0.5T, the diameter of a bore is 1 m, and the uniformity of the magnetic field is 5 ppm/30 cm dsv (sphere).

A person which is to be inspected, lies on a patient table 5, and is moved to a central portion of the magnet 1. A gradient magnetic field for obtaining spatial position information is superposed on a static magnetic field formed by the magnet 1. A radio-frequency (RF) signal for generating nuclear magnetic resonance (NMR) is sent from a transmitter 7 to an irradiation coil 3, and an NMR signal generated by the to-be-inspected person or material is detected by a receiving coil 4, to be sent to a receiver 8. The phase information of the NMR signal is important in NMR imaging. Hence, the signal phase in the receiver 8 is accurately synchronized with the signal phase in the transmitter 7 by a receiver gate signal 12.

A gradient magnetic field source 9 includes three magnetic field generators for generating gradient fields in X-, Y- and Z-directions independently of each other. Since each of the gradient fields is applied to the to-be-inspected person in the form of a pulse, the magnetic field generators are required to have rapid response characteristics. The generation of the pulse is controlled by a gradient field controller 20.

The MRI apparatus is operated with the aid of an operation desk 10 provided with two CRT display devices, in addition to various keys. One of the CRT display devices is used for setting various parameters in an interactive mode, and for operating the MRI apparatus, and the other display device is used for displaying a tomogram.

High-speed arithmetic operations for controlling the MRI apparatus and for forming the tomogram are performed by a computer 90. Signals are transferred between the computer 90 and controllers through a bus 17. Various pulse sequences are controlled by a sequence controller 16. The combination of the RF pulse and the gradient field pulses is the most important pulse sequence.

The fundamental items of the imaging method utilizing nuclear magnetic resonance will be explained, with reference to FIGS. 5 and 6.

Figure 5:
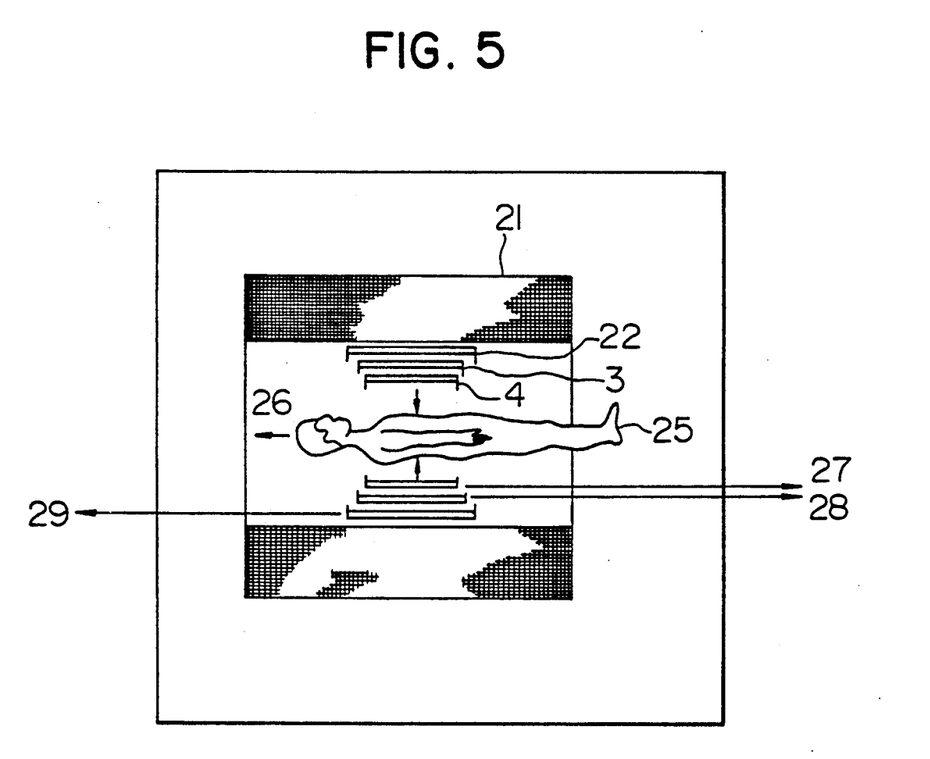
FIG. 5 is a sectional view showing the measuring part of the MRI apparatus of FIG. 4.

FIG. 5 is a sectional view showing the measuring part of the MRI apparatus. The super-conducting magnet of FIG. 4 is formed of a super-conducting static field coil 21 kept at a helium temperature for generating a static magnetic field. A gradient field coil 22, an irradiation coil 3 and a receiving coil 4 are disposed inside of the static field coil 21. The direction of the static magnetic field is indicated by an arrow 26 in FIG. 5. Usually, the direction of the static magnetic field is defined as a Z-direction. In order to generate three gradient magnetic field in X-, Y- and Z-directions independently of each other, three coils for X-gradient field, Y-gradient field and Z-gradient field are disposed in the MRI apparatus.

Figure 6:
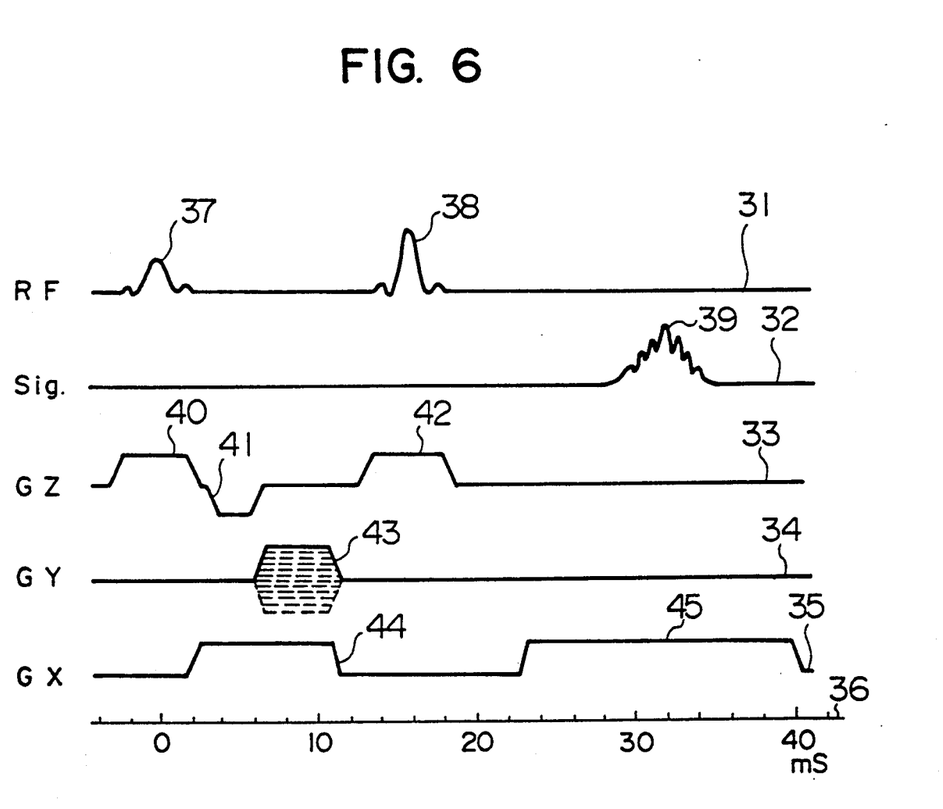
FIG. 6 is a waveform chart showing a pulse sequence which is used for the MRI apparatus.

FIG. 6 shows an example of the pulse sequence used for forming a tomogram. In FIG. 6, reference numeral 31 designates the waveform of an RF pulse which is supplied from the irradiation coil to the to-be-inspected person, 32 the waveform of a signal which is obtained by amplifying the electromotive force of the receiving coil, 33 the waveform of a pulse for forming a gradient magnetic field in the direction of the static magnetic field, 34 the waveform of a pulse for forming a gradient magnetic field in the Y-direction to encode a phase, 35 the waveform of a pulse for forming a gradient magnetic field in the X-direction to cause a coordinate value in the X-direction to correspond to a resonance frequency on a one-to-one basis, and 36 a time axis for indicating the timing of each pulse or signal. In general, the gradient magnetic field in the X-direction is used for generating a spin echo, and is therefore regarded as the read gradient field.

Next, the function of each pulse will be explained in more detail, and the principle of an image constructing method which is called "two-dimensional Fourier method", will be explained.

In the pulse sequence of FIG. 6, the RF pulse has the form of a sinc function. Element 42 corresponds to a gradient field pulse; Element 43 corresponds to a phase encoded gradient magnetic field; element 44 corresponds to a frequency encoded gradient magnetic field, and element 45 corresponds to a read out gradient magnetic field. When Fourier transform is carried out for the sinc function, a rectangular waveform is obtained. That is, a sinc function in a time space is converted into a rectangular waveform in a frequency space. Thus, the RF pulse having the form of a sinc function has frequencies in a limited range. In FIG. 6, a gradient field pulse 40 for forming a gradient magnetic field in the Z-direction is applied to a coil at the same time as a 90° pulse (for inclining a nuclear spin by an angle of 90°) is applied to the irradiation coil. The resonance condition in nuclear magnetic resonance is given by the following equation:

$$\omega_0 = \gamma[H_0 + H_G(Z)] \tag{1}$$

where $\omega_0$ indicates an angular velocity at a resonance point, $\gamma$ the gyromagnetic ratio, $H_0$ the flux density of the static magnetic field, and $H_G(Z)$ the flux density of the gradient magnetic field at a position having a coordinate value Z. As can be seen from the equation (1), only a specified cross section (that is, specified slice) perpendicular to the Z-direction is excited.

In an ordinary MRI apparatus, the frequencies of the 90° pulse are set so that the slice has a thickness of 1 to 20 mm. In the pulse sequence of FIG. 6, a 180° pulse 38 is applied to the irradiation coil after the 90° pulse 37 was applied thereto, to obtain a spin echo signal 39. It is to be noted that in the original, two-dimensional Fourier method, a spin echo is generated by a gradient magnetic field, without using the 180° pulse.

The spin echo technique is the technique for making uniform the phase of nuclear spin which rapidly dispersed with an apparent transverse relaxation time $T_2$ on the basis of a non-uniform magnetic field, after a predetermined time has elapsed. A gradient magnetic field is a non-uniform magnetic field of a kind. In order to obtain a signal based upon the nuclear spin with the same phase, it is necessary to reverse the gradient magnetic field, or to generate the 180° pulse together with the gradient magnetic field. In fact, it takes a definite time (for example, about 1 millisecond) to generate or eliminate the gradient magnetic field. In this period of transition, the phase of nuclear spin is disordered. In order to compensate for the phase disorder, a compensation pulse 41 is applied to a coil after a gradient field pulse 40 has been applied thereto. Thus, the phase disorder at the leading and falling edges of the gradient field pulse 40 is cancelled. That is, the combination of the pulses 40 and 41 is equivalent to a rectangular gradient field pulse.

Next, phase encoding will be explained. The fundamental properties for determining the behavior of a nuclear spin are the direction of a magnetic moment, the magnitude of the magnetic moment, the number of magnets each caused by a magnetic moment, the perturbation frequency of a magnetic moment, and the phase of perturbation of the magnetic moment. The behavior of macroscopic magnetization is given as the statistical results of the above parameters. Specifically, the above-mentioned frequency and phase are independent of each other, and the frequency can be made correspond to a space coordinate by encoding the phase. A gradient magnetic field for encoding the phase is the gradient magnetic field 34 in the Y-direction shown in FIG. 6. The amount of phase encoding is determined by an integrated value of the encoding, gradient field pulse, and thus can be varied by changing a pulse amplitude or pulse width. In the pulse sequence of FIG. 6, the pulse amplitude is changed.

A gradient magnetic field 35 in FIG. 6 is a gradient magnetic field in the X-direction. When the gradient magnetic field in the X-direction is applied to nuclear spins which have been excited by the 90° pulse 37 and make coherent precession, the frequency of precession is changed linearly in the X-direction. When the gradient magnetic field in the X-direction is again applied to the nuclear spins after the 180° pulse 38 has been applied thereto, the spin echo signal 39 can be obtained. As can be seen from the above, a resonance frequency varies linearly with an X-coordinate. Accordingly, when Fourier transform is carried out for the spin echo signal, the X-coordinate dependence of signal intensity is known. When Fourier transform with respect to the phase-encoding direction (that is, Y-direction) is carried out for the result of the above transform, the Y-coordinate dependence of signal intensity is known. Thus, the distribution of signal intensity on an X-Y plane are obtained. When this distribution is displayed on the display screen of a CRT display device, a tomogram is obtained.

Usually, it takes a time of a few minutes to 20 minutes to form the tomogram of an internal tissue or focus (namely, lesion) in the above-mentioned manner. When a physical portion to be imaged moves in the above time, the picture quality of the tomogram of the to-be-imaged physical portion is greatly degraded.

Specifically, the abdominal region moves with breathing. Accordingly, the abdominal region is not suited to be imaged by the MRI method.

Figure 1A:
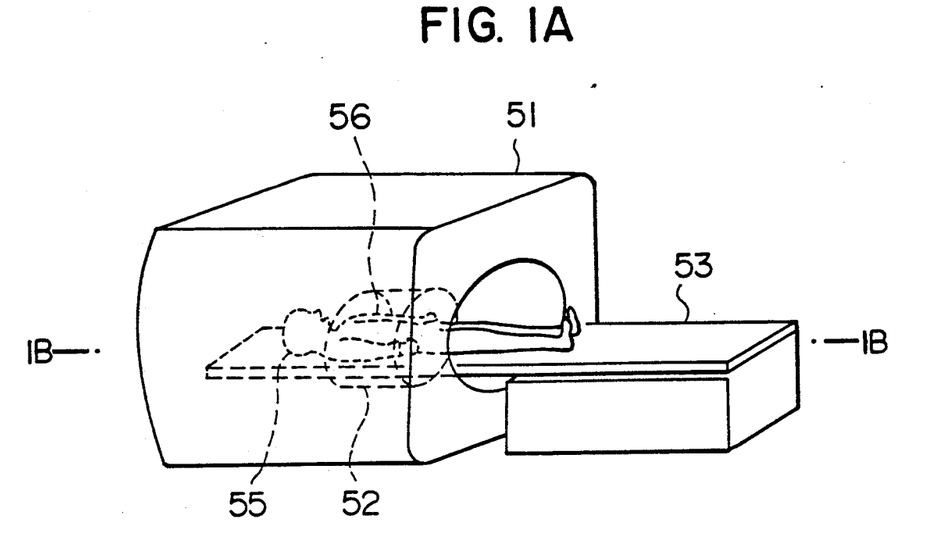
FIG. 1A is a perspective view showing an MRI apparatus in which the abdominal region of a person is inspected.
Figure 1B:
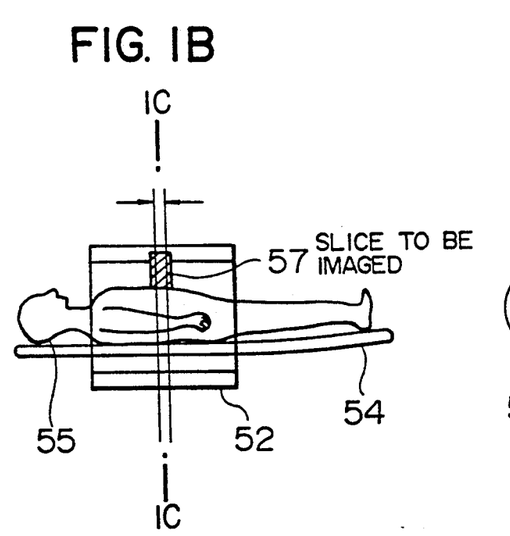
FIG. 1B is a sectional view which shows an embodiment of an inspection method according to the present invention and corresponds to a sectional view taken along the line 1B—1B of FIG. 1A.
Figure 1C:
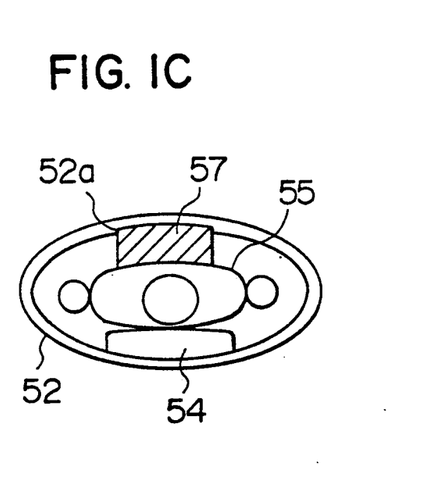
FIG. 1C is a sectional view taken along the line 1C—1C of FIG. 1B.

FIGS. 1A to 1C show an MRI apparatus which can suppress the movement of a portion of the abdominal region due to breathing, at a time the portion is imaged. In other words, FIGS. 1B and 1C show an embodiment of an inspection method according to the present invention.

Figure 1D:
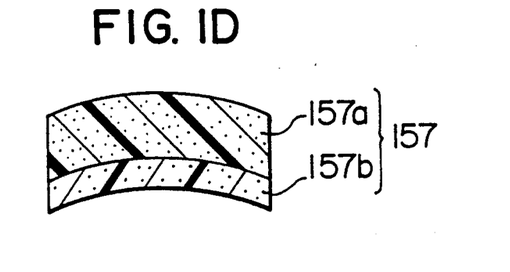
FIG. 1D is a sectional view showing a modified version of an elastic body shown in FIGS. 1B and 1C.

In the MRI apparatus, an elastic body 57 is interposed between a person 55 to be inspected and a coil 52, on a plane including a slice to be imaged, and the elastic body 57 is put in a slightly compressed state. In view of the intensity distribution of magnetic field, the to-be-imaged slice is usually disposed in a central portion of the coil 52. A groove 52a for attaching the elastic body 57 to the coil 52 is formed in a central region of the inner surface of the coil 52 in a circumferential direction. The elastic body 57 is formed of a sponge. However, the elastic body 57 is not limited to the sponge, but may be made of various materials capable of applying a pressure of 1 to 100 g/cm² on a to-be-inspected person 55. It is preferable that the elastic body has a width of less than 15 cm. If the width of the electric body is not less than 15 cm, the movement of a physical portion to be imaged cannot be suppressed. FIG. 1D shows a modified version 157 of the elastic body 57. The modified elastic body 157 is made up of a portion 157a which is relatively hard, that is, has a form keeping ability, and another portion 157b which is relatively soft and is put in contact with the to-be-inspected person 55. By fitting the portion 157a to the groove 52a, the modified elastic body 157 is accurately located in relation to the to-be-inspected person 55.

Such elastic bodies apply a pressure of, for example, 1 to 100 g/m² on the surface of the to-be-inspected person 55, to make the circumstances at the pressure applied surface area different from the circumstances at the remaining surface area, thereby causing the already-mentioned phenomenon. Various members having different shapes and made of different materials can be used as an elastic body, provided that the phenomenon is caused by the members. In FIGS. 1B and 1C, the elastic body 57 is pressed against only the upper surface of the abdominal region. Alternatively, the whole exposed surface of the to-be-imaged slice may be covered with the elastic body 57. Further, the portion 157a of the modified elastic body 157 may be formed of a rigid body.

By using the elastic body 57 or 157, a physical portion moving with breathing is changed from the abdominal region to the breast. Thus, the to-be-imaged physical portion will hardly move.

Figure 2A:
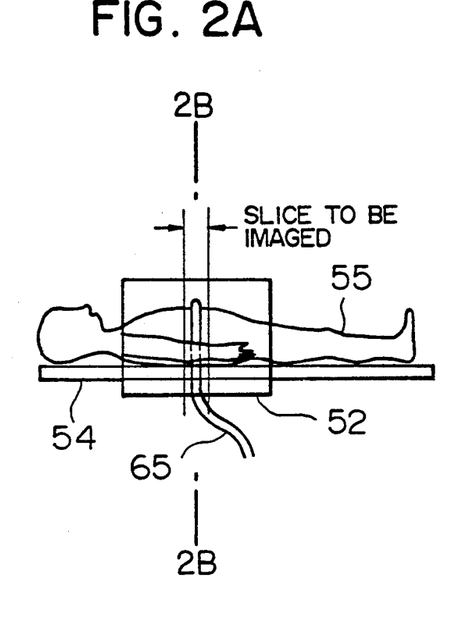
FIG. 2A is a sectional view showing another embodiment of an inspection method according to the present invention.
Figure 2B:
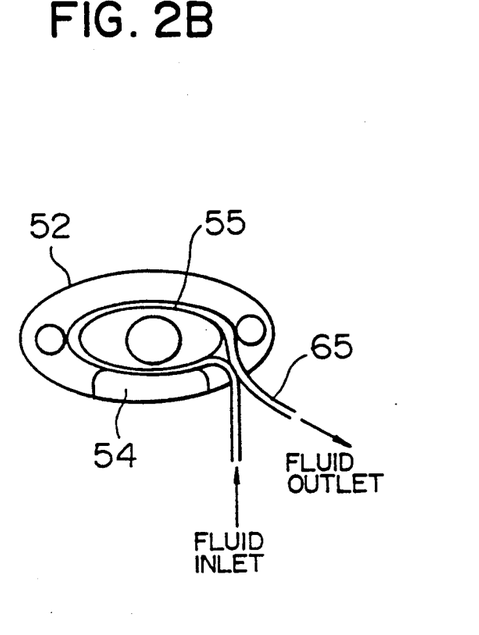
FIG. 2B is a sectional view taken along the line 2B—2B of FIG. 2A.

FIGS. 2A and 2B show another embodiment of an inspection method according to the present invention, in which embodiment the movement of the to-be-imaged portion is suppressed by giving a temperature stimulus to the surface of the to-be-imaged portion. Referring to FIGS. 2A and 2B, warm water having a temperature (for example, about 43° C.) higher than the bodily temperature, or cold water having a temperature of 15° to 20° C. flows through a soft, elastic tube 65. The tube 65 is wound around the to-be-imaged slice. In this case, the to-be-inspected person 55 feels a temperature difference, and a moving portion due to breathing, is unconsciously spaced apart from the to-be-imaged portion. Further, the to-be-inspected person 55 knows a physical portion which corresponds to an imaging position and should not be moved, on the perception of the temperature difference, and consciously endeavors to keep the physical portion quiet.

Figure 3A:
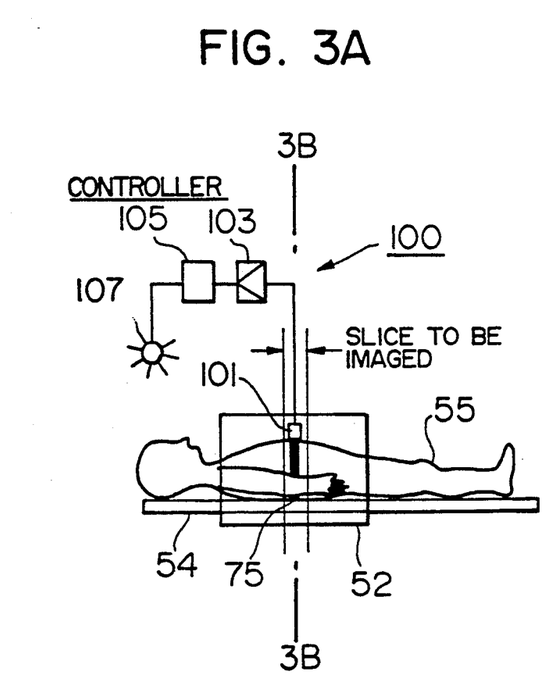
FIG. 3A is a sectional view showing a further embodiment of an inspection method according to the present invention.
Figure 3B:
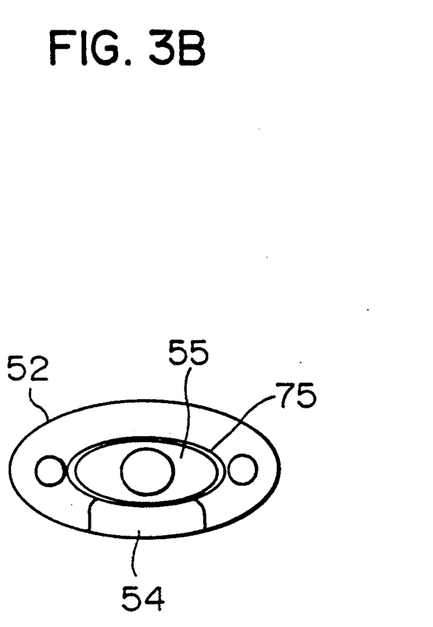
FIG. 3B is a sectional view taken along the line 3B—3B of FIG. 3A.

FIGS. 3A and 3B show a further embodiment of an inspection method according to the present invention, in which embodiment the movement of a to-be-imaged portion is suppressed by giving a rough feel to the surface of the to-be-imaged portion. In this case, a belt 75 capable of expansion and contraction is wound around the surface of the to-be-imaged portion. The inner surface of the belt 75 (that is, that surface of the belt 75 which is put in direct contact with the surface of the to-be-imaged portion) is made rough. When the surface of the to-be-imaged portion is rubbed with the rough surface of the belt by the movement of the to-be-imaged portion due to breathing, the to-be-inspected person feels that the to-be-imaged portion of the abdominal region is rubbed with a rough surface, and unconsciously breathes not by moving the abdominal region but by moving the breast. Further, the to-be-inspected person can consciously breathe so that the rubbing at the to-be-imaged portion is not felt, to keep the to-be-imaged portion quiet. In the present embodiment, it is necessary to make rough at least that area of the inner surface of the belt 75 which is put in contact with the upper side of the abdominal region.

Further, as shown in FIG. 3A, a movement indicating device 100 can be attached to the MRI apparatus. The movement indicating device 100 is made up of a sensor 101, an amplifier 103, a controller 105 and a lamp 107. The sensor 101 delivers a signal having an amplitude which corresponds to the movement of the to-be-imaged portion. The signal is applied by the amplifier 103, which delivers an amplified signal to the controller 105. The controller 105 controls a current which is supplied to the lamp 107, in accordance with the amplified signal, to make the brightness of the lamp 107 correspond to the movement of the to-be-imaged portion. Thus, the to-be-inspected person knows the state of the to-be-imaged portion from the brightness of the lamp 107, and can consciously control breathing so that the lamp 107 becomes dark.

The present invention is not only used for suppressing the movement of a physical portion due to breathing, but also can be used for suppressing the movement of a physical portion due to another physiological phenomenon.

For example, the present invention is applicable to a case where a false image (an artifact) is formed on the tomogram of the neck region on the basis of the unconscious movement of the neck portion caused by gulping spit. In this case, movement suppressing means similar to that for the abdominal region is used for the neck region.

As has been explained in the foregoing, according to the present invention, the movement of a to-be-imaged portion and its neighborhood is suppressed. Thus, it is possible to form an accurate tomogram of a abdominal tissue or focus which has not been accurately imaged.

What is claimed is:

1. An inspection method utilizing nuclear magnetic resonance for inspecting an object in a physical portion of a patient which physical portion has physiological movement, comprising the steps of:
    stimulating the patient in at least a part of an area of a surface of the physical portion of the patient having physiological movement which exists on a plane indicative of a slice including the object to be inspected to cause the patient to suppress the physiological movement in said stimulated part, said stimulating being accomplished without tight binding or pressing the portion; and
    forming a tomogram of the object to be inspected by using the nuclear magnetic resonance while said physiological movement is suppressed.

2. An inspection method according to claim 1, wherein the step of forming the tomogram comprising the steps of:
    (a) exciting a nuclear spin in the slice of the object to be inspected, including generating a pulse for forming a slice-selecting, gradient magnetic field in a first direction perpendicular to the slice;
    (b) encoding a phase of the nuclear spin with positional information by generating a pulse for forming a phase-encoding, gradient magnetic field in a second direction, to generate a desired nuclear magnetic resonance signal;
    (c) obtaining the nuclear magnetic resonance signal when a pulse for generating a read gradient magnetic field in a third direction is generated;
    (d) repeating the steps (a) to (c) while changing the intensity-time product of the pulse for forming the phase-encoding, gradient magnetic field; and
    (e) carrying out multi-dimensional Fourier transform for each of nuclear magnetic resonance signals, to form a tomogram on the basis of the spin distribution obtained from each nuclear magnetic resonance signal.

3. An inspection method according to claim 1, wherein the step of stimulating the patient include generating a different pressure on said at least a part of the area of the surface of the physical portion which corresponds with the slice of the object to be inspected, than a pressure on the surface of a remaining physical portion of the patient.

4. An inspection method according to claim 3, wherein the step of generating the different pressure includes the step of generating a pressure at the surface of the physical portion which corresponds with the slice of the object to be inspected, by a restoring force of an elastic body which has been previously compressed.

5. (Twice Amended) An inspection method according to claim 3, wherein the step of generating the different pressure includes a step of generating a different pressure on at least the part of the area of the surface of the physical portion which corresponds with the slice of the object to be inspected, by a restoring force of an organic, synthetic foam material which has been previously compressed.

6. An inspection method according to claim 1, wherein said stimulating includes making the temperature of at least a part of the area of the surface of the physical portion which agrees with the slice including the to-be-inspected object, different from the temperature of the surface of the remaining physical portion.

7. An inspection method according to claim 1, wherein the stimulating includes contacting said at least a part of the area of the surface of the physical portion which agrees with the slice including the to-be-inspected object with a rough surface of a device so that the patient feels differently in the area contacted as compared with the feel at the surface of the remaining physical portion.

8. An inspection method according to claim 1, wherein the step of stimulating the patient is accomplished by pressing the portion with a pressure less than 100 g/cm$^2$.

9. An inspection apparatus for inspecting an object in a physical portion of a patient which physical portion has physiological movement, by utilizing nuclear magnetic resonance, the inspection apparatus comprising:
    means for stimulating the patient in at least a part of an area of a surface of the physical portion of the patient having said physiological movement which exists on a plane indicative of a slice including the object to be inspection to cause the patent to suppress said physiological movement, said stimulating means acting on said patient without tight binding or pressing the portion
    means for exciting the nuclear spin in the slice of the object to be inspected, including generating a pulse for forming a slice-selecting, gradient magnetic field in a first direction perpendicular to the slice;
    means for encoding a phase of the nuclear spin with positional information by generating a pulse for forming a phase-encoding, gradient magnetic field in a second direction, to generate a desired nuclear magnetic resonance signal;

means for obtaining the nuclear magnetic resonance signal when a pulse for generating a read gradient magnetic field in a third direction is generated;

means for changing the intensity-time product of the pulse for forming the phase-encoding, gradient magnetic field; and means for carrying out multi-dimensional Fourier transform for the nuclear magnetic resonance signal, to form a tomogram on the basis of the spin distribution obtained from each of a plurality of nuclear magnetic resonance signals corresponding to different values of the intensity-time product of the pulse for forming the phase-encoding, gradient magnetic field.

10. An inspection apparatus according to claim 9, wherein the stimulating means includes means for generating a different pressure at said at least part of the area of the surface of a physical portion which corresponds to the slice of the object to be inspected, than a pressure at the surface of a remaining physical portion of said patient.

11. An inspection apparatus according to claim 9, wherein said stimulating means makes the temperature of said at least part of the area of the surface of said physical portion which agrees with the slice including the to-be-inspected object, different from the temperature of the surface of the remaining physical portion.

12. An inspection apparatus according to claim 9, wherein said stimulating means makes the patient's feeling at said at least part of the area of the surface of the physical portion which agrees with the slice including the to-be-inspected object, different from the feeling at of the remaining surface of the physical portion through the application of a rough surface of said stimulating means on said at least part of the area of the surface of the physical portion.

13. An inspection apparatus according to claim 9, further comprising means for informing the patient of the movement of the physical portion.

14. In combination, a nuclear magnetic resonance inspection apparatus for inspecting an object in a physical portion of a patient utilizing nuclear magnetic resonance, said apparatus including a part having an inner surface adapted to be arranged around the physical portion of the patient during inspection, said inner surface having a groove formed therein, and an imaging-operation assisting device comprising first means for stimulating the patient in at least a part of an area of a surface of said to-be-inspected physical portion to cause the patient to suppress the physiological movement, said stimulating being accomplished without tight binding and without pressing the portion; and second means for fixing the first means at a position where the first means is placed on said at least part of the area of the surface of physical portion which corresponds to the to-be-imaged slice, wherein said second means includes a connecting member connected to said first means and adapted to be inserted into the groove in the inner surface of said part of the inspection apparatus.

* * * * *